(12) United States Patent
Matyjaszewski et al.

(10) Patent No.: US 6,288,186 B1
(45) Date of Patent: Sep. 11, 2001

(54) RATE ENHANCEMENT OF NITROXYL RADICAL-MEDIATED POLYMERIZATION

(75) Inventors: Krzysztof Matyjaszewski; Dorota Greszta, both of Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 09/200,470

(22) Filed: Nov. 27, 1998

Related U.S. Application Data

(62) Division of application No. 08/701,437, filed on Aug. 22, 1996, now Pat. No. 5,910,549.

(51) Int. Cl.[7] .......................................................... C08F 2/00
(52) U.S. Cl. .......................... 526/220; 526/217; 526/227; 526/230; 526/236
(58) Field of Search .................................... 526/220, 217, 526/236, 227, 230

(56) References Cited

U.S. PATENT DOCUMENTS

| | | |
|---|---|---|
| 3,862,978 | * 1/1975 | Decker et al. . |
| 4,145,486 | * 3/1979 | Haag et al. . |
| 4,581,429 | 4/1986 | Solomon et al. . |
| 5,169,914 | * 12/1992 | Kaszas et al. . |
| 5,322,912 | 6/1994 | Georges et al. . |
| 5,401,804 | 3/1995 | Georges et al. . |
| 5,405,913 | * 4/1995 | Harwood et al. . |
| 5,451,647 | * 9/1995 | Faust et al. . |
| 5,677,388 | 10/1997 | Koster et al. . |
| 5,708,102 | * 1/1998 | Fryd et al. . |
| 5,763,548 | 6/1998 | Matyjaszewski et al. . |
| 5,767,210 | * 6/1998 | Lecomte et al. . |
| 5,773,538 | * 6/1998 | Feiring . |
| 5,789,487 | 8/1998 | Matyjaszewski et al. . |
| 5,807,937 | 9/1998 | Matyjaszewski et al. . |
| 5,811,500 | * 9/1998 | Dubois et al. . |
| 5,854,364 | * 12/1998 | Senninger et al. . |

FOREIGN PATENT DOCUMENTS

| | | |
|---|---|---|
| 1165828A | * 11/1997 | (CN) . |
| 0 265 091 A1 | * 4/1988 | (EP) . |
| 0 789 036 A2 | * 8/1997 | (EP) . |
| 0 816 385 A1 | * 1/1998 | (EP) . |
| 0 824 110 A1 | * 2/1998 | (EP) . |
| 0 824 111 A1 | * 2/1998 | (EP) . |
| 0 826 698 A1 | * 3/1998 | (EP) . |
| 0 832 902 A2 | * 4/1998 | (EP) . |
| WO 97/47661 | * 12/1997 | (WO) . |
| WO 98/06758 | * 2/1998 | (WO) . |
| WO 98/20050 | * 5/1998 | (WO) . |

OTHER PUBLICATIONS

Polymer Letters, vol. 5, pp. 697–701, 1967, New Initiator Systems for Radical Polymerization of Vinyl Monomers, Takayuki Otsu et al.*

Science, vol. 272, pp. 866–868, May 10, 1996, Polymers With Very Low Polydispersities From Atom Transfer Radical Polymerization, Timothy E. Patten et al.*

Macromolecules, vol. 31, No. 12, 1998, pp. 4053–4056, Self–Regulated Phase Transfer of $Cu_2O$/bpy, Cu(0)/bpy, and $Cu_2O$/Cu(0)/bpy Catalyzed "Living" Radical Polymerization Initiated With Sulfonyl Chlorides, V. Percec et al.*

J. Chem. Soc. (B), pp. 255–259, Redox–Transfer, Part VI, Determination of Hammet's ρConstant for the Oxidation of Cuprous Chloride by Aromatic Sulphonyl Chlorides, A. Orochov et al.*

Asscher and Vofsi, pp. 4962–4971, Chlorine–Activation by Redox–Transfer, Part IV. The Addition of Sulphonyl Chlorides to Vinylic Monomers and Other Olefins, M. Asscher et al.

J. Chem. Soc. Perkin Trans, 1991, pp. 627–633, Novel Perfluoroalkylation of Alkenes with Perfluoroalkanesulphonyl Chlorides Catalysed by a Ruthenium (II) Complex, Nobumasa Kamigata et al.

Macromolecules, vol. 28, No. 23, 1995, pp. 7970–7972, "Living" Radical Polymerization of Styrene Initiated by Arenesulfonyl Chlorides and $Cu^1(bpy)_nC1$, Virgil Percec et al.

(List continued on next page.)

Primary Examiner—Fred Zitomer
(74) Attorney, Agent, or Firm—Kirkpatrick & Lockhart LLP

(57) ABSTRACT

An improved process for free radical polymerization is produced making it possible to control the growth steps of a polymerization to produce homopolymers and copolymers, including block and graft copolymers. The process uses a long half-life radical initiators and compounds which have the structure of formula I

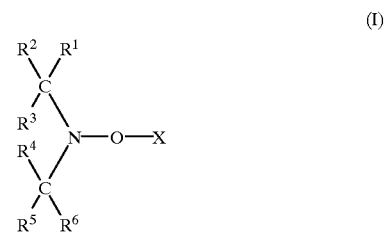

(I)

wherein X is a group having at least one carbon atom and is such that the free radical X. is capable of polymerizing the unsaturated monomer by free radical polymerization, and the radical functionality resides on the or one of the carbon atoms, $R^1$, $R^2$, $R^5$ and $R^6$ represent the same or different straight chain or branched substituted or unsubstituted alkyl groups of a chain length sufficient to provide steric hindrance and weakening of the O—X bond, and $R^3$ and $R^4$ represent the same or different, straight chain or branched, substituted alkyl groups or $R^3CNCR^4$ may be part of a cyclic structure which may have fused with it another saturated or aromatic ring, the cyclic structure or aromatic ring being optionally substituted.

53 Claims, 3 Drawing Sheets

OTHER PUBLICATIONS

Macromolecules, vol. 29, No. 10, 1996, pp. 3665–3668, Metal–Catalyzed "Living" Radical Polymerization of Styrene Initiated with Arenesulfonyl Chlorides. From Heterogeneous to Homogeneous Catalysis, Virgil Percec et al.

Chemical Abstracts, vol. 85, 1976, pp. 20.

Science, vol. 25, Feb. 22, 1991, pp. 887–893, Living Polymerization Methods, Owen W. Webster.

Journal of Polymer Science: Part A: Polymer Chemistry, vol. 36, 1417–1424, 1998, Polymerization of Acrylates by Atom Transfer Radical Polymerization Homopolymerization of 2–Hydroxyethyl Acrylate, Simion Coca et al.

Macromolecules, vol. 29, No. 27, 1996, 8576–8582, Controlled Radical Polymerization of Methacrylic Monomers in the Presence of Bis(Ortho–Chelated) Arylnickel(II) Complex and Different Activated Alkyl Halides, C. Granel, et al.

Macromolecules, vol. 30, No. 23, 1997, 7348–7350, Zerovalent Metals in Controlled/"Living" Radical Polymerization, Krzysztof Matyjaszewski et al.

Macromolecules, vol. 31, No. 12, 1998, 4041–4044, Nitroxide Mediated Living Radical Polymerization of Styrene in Emulsion, Catherine Marestin et al.

Macromolecules, vol. 30, No. 25, 1997, 7692–7696, Controlled/"Living" Radical Polymerization Homogenous Reverse Atom Transfer Radical Polymerization Using Aibn as the Initiator, Jianhui Xia et al.

Macromolecules, vol. 30, No. 2, 1997, 324–326, Controlled Radical Polymerization in Emulsion, Stefan A.F. Bon et al.

Macromolecules, vol. 30, No. 8, 1997, 2244–2248, Evidence for Living Radical Polymerization of Methyl Methacrylate with Ruthenium Complex: Effects of Protic and Radical Compounds and Reinitiation from the Recovered Polymers, Tomotaka Nishikawa et al.

Controlled Atom Transfer Radical Polymerizations of Methyl Methacrylate Under Micellar Conditions, Takayuki Makino et al. pp. 288–289.

Part 2, Controlled "Living" Emulsion Polymerization of Methyl Methacrylate by Atom Transfer Radical Polymerization, pp. 90–134.

Matyjaszewski, K., "The Importance of Exchange Reaction sin the Controlled/Living Radical Polymerization in the Presence of Alkoxyamines and Transition Metals":, Macromolecule Symposium, 1996, vol. 111, pp. 47–61.

Georges, M.K., Veregin, R.P.M.; Kazmaier, P.M.; Hamer, G.K. Macromolecules 1993, 26, 2987.

Mardare, et al., ACS Polymer Preprints 1994 35(1), 778.

Ledine et al., J. Am. Chem. Soc. 1996, 118, pp. 11111–11118.

Li et al., ASC Polym. Prperints 1995, 35(1) 469.

Catala et al., Macromolecules 1995, 28, 8441.

Puts et al., Macromolecules 1996, 29, 3323.

Hawker et al., Macromolecules 1996, 29, 2686.

Fukuda et al., Macromolecules 1996, 29, 3050.

Veregin et al., Macromolecules 1996, 29, 2746.

Fisher, Am. Chem. Soc. 1986, 108, 3925.

Georges et al., Macromolecules 1994, 27, 7228.

Odell et al., Macromolecules 1995, 28, 8453.

Veregin et al., Macromolecules 1996, 29, 4161.

Georges et al, Macromolecules 1993, 26, 5316.

* cited by examiner

RATE ENHANCEMENT OF NITROXYL RADICAL-MEDIATED POLYMERIZATION

This application is a division of application Ser. No. 08/701,437, Aug. 22, 1996, U.S. Pat. No. 5,910,549.

BACKGROUND OF THE INVENTION

1. Field of the Invention

The invention is directed to a method of enhancing the rate of polymerization of nitroxyl radical-mediated polymerization of unsaturated monomers. More particularly, the invention is directed to the rate enhancement of radical polymerization in the presence of the 2,2,6,6-tetramethyl-1-piperidinoxyl radical (TEMPO).

2. Discussion of the Background

The concept of applying stable nitroxyl radicals to control free-radical polymerization was developed by Solomon and Rizzardo[1] for a variety of monomers, but this original approach was limited to low molecular weight polymers. Subsequently, Georges et al adapted this approach to polymerization of styrene initiated by benzoyl peroxide in the presence of TEMPO[2] yielding high molecular weight polymers with narrow polydispersities and molecular weights linearly increasing with conversion. Other groups have reported that well-defined polymers can also be obtained in thermal polymerization of styrene in the presence of TEMPO[3] as well as in the polymerization of styrene initiated by various TEMPO adducts[4,5] and other alkoxyamines[6,7]. Additionally, copolymers of styrene and other vinyl monomers have also been synthesized in a controlled manner by using this techniques[8,9].

The control of the polymerization is achieved by reversible scavenging of the propagating radicals by a stable nitroxyl radical:

Scheme I

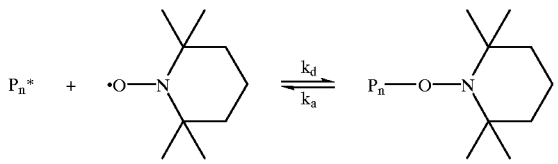

The above equilibrium is shifted strongly to the right side and thus the concentration of the active species is lower in the TEMPO-moderated polymerization than in a conventional free radical polymerization. Consequently, the rate of bimolecular termination, which is second order with respect to radical concentration, is lower and does not lead to a broadening of the molecular weight distributions, in contrast to conventional polymerizations. However, the rate of propagation (first order with respect to radical concentration) is also affected, although much less than the termination.

The long time required for completion of polymerization, even at relatively high temperatures and independently of the initiator concentration, is the most important disadvantage of this process. For example, bulk polymerization of styrene takes 20 hrs. to reach 60% conversion and 44 hrs. to reach final conversion at 120° C. for a TEMPO adduct concentration of 0.01M. The reason for the slow polymerization rate is a low stationary concentration of the propagating radicals. At 120° C., the equilibrium constant $K=[P^*]\cdot([T^*]/[PT])$, where $P^*$ is propagating radicals, $T^*$ is free TEMPO and PT is TEMPO-capped dormant chains, is on the order of $10^{-11}$ mol.L$^{-1}$. The experimentally determined stationary concentration TEMPO is on the order of 0.1% of the original concentration of TEMPO or its adduct[11,12]. Thus, the stationary concentration of propagating radicals is on the order of $10^{-8}$ mol.L.

The rate of the polymerization of styrene in the presence of TEMPO is independent of the concentration of the initiator and remarkably close to the rate of thermal polymerization under similar conditions. It has been shown that it is thermal self-initiation of styrene that provides a concentration of propagating radicals sufficient for obtaining reasonable, albeit slow, polymerization rates[11]. If the thermal initiation were absent, the polymerization would be even slower. Based on the above observations, a conclusion might be drawn that the rate of the TEMPO-mediated polymerization of styrene can be enhanced by decreasing the concentration of TEMPO and thereby, increasing the concentration of propagating radicals. Since the polymerization is controlled by the excess of TEMPO (a persistent radical effect[14]), this approach would undoubtedly lead to a higher rate of bimolecular termination and an increase of polydispersities if the concentration of TEMPO is brought too low and the rate of the trapping of the growing chains becomes lower than the rate of propagation. This might be avoided if the concentration of radicals is only few times higher than the concentration of radicals provided by thermal self-initiation, and the excess of TEMPO is continuously but slowly being removed from the system.

Georges et al reported that addition of a small amount of camphorsulfonic acid (CSA)[15] or 2-fluoro-1-methylpyridinium p-toluenesulfonate[16] to a polymerization of styrene initiated by benzoyl peroxide in the presence of TEMPO increased the rate of polymerization significantly. But the addition of CSA or the salt also caused a broadening of polydispersities, particularly at the beginning of the polymerization. In the case of CSA as an additive, Georges et al postulated that the excess of TEMPO is removed by a rapid reaction with CSA[17]. This reaction irreversibly eliminates some of the nitroxide present at the beginning of the polymerization, thereby reducing the induction period. After the initial increase in the rate, the polymerization proceeds with virtually unchanged rate[15]. The mechanism of the rate enhancement in the presence of the salt is unknown so far.

A need continues to exist, therefore, for improved methods of controlling the rate of nitroxyl radical-mediated polymerization.

SUMMARY OF THE INVENTION

Accordingly, one object of the present invention is to provide a method for the rate enhancement of nitroxyl radical-mediated polymerization. This and other objects which will become apparent in the course of the following specification have been achieved by the present method for the production of polymers by free radical polymerization of suitable unsaturated monomers in the presence of a radical initiator with a long half-life at the reaction temperature and a compound having the formula (I)

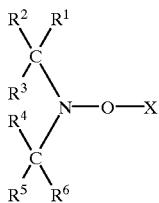

(I)

wherein

X is a group comprising at least one carbon atom and is such that the free radical X. is capable of polymerizing the unsaturated monomer by conventional free radical polymerization, and the radical functionality resides on one of the carbon atoms, and the groups $R^1$, $R^2$, $R^5$ and $R^6$ are the same or different, straight chain or branched, substituted or unsubstituted alkyl groups of a chain length sufficient to provide steric hindrance and weakening of the O—X bond, and $R^3$ and $R^4$ are the same or different, straight chain or branched alkyl or substituted alkyl groups or the portion $R^3CNCR^4$ may be part of a cyclic structure which may have fused with it another saturated or aromatic ring.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
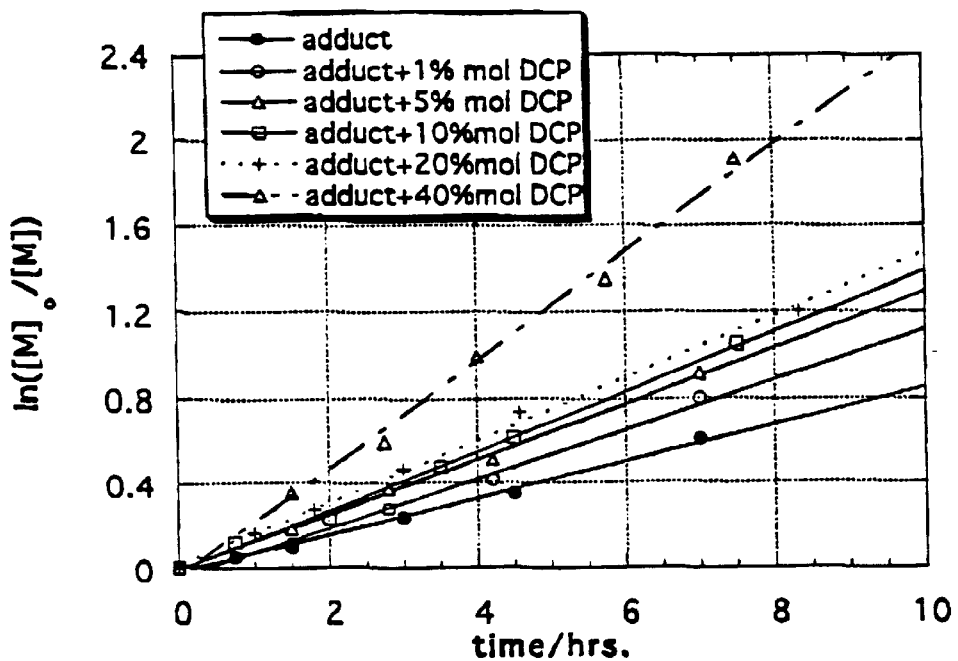
FIG. 1 shows kinetic plots of $\ln([M]_o/[M])$ vs. time for bulk polymerization of styrene in the presence of 1-phenylethyl-TEMPO adduct (0.010M) and variable amounts of dicumyl peroxide (DCP); temperature 120° C.

In this invention an alternative approach to rate enhancement of nitroxyl radical-mediated polymerization has been discovered. In this approach the increase in polymerization rate is achieved by adding a small amount of a radical initiator with a long half-life time at the reaction temperature. In this system, the excess of nitroxyl radical is continuously decreased by reaction with radicals formed by a slowly decomposing radical initiator, in analogy to thermal self-initiation. Preferably, the initiator is employed at concentrations such that it decomposes with a rate comparable to the rate of initiation of thermal polymerization of styrene under the polymerization conditions.

In the present invention, "a radical initiator with a long half-life time" means a radical initiator with a half-life time comparable to the polymerization half-life time and used in such amount that the total concentration of radicals produced by its decomposition does not exceed 30% of a sum of initial amount of nitroxyl radical (II) and alkoxyamine used (I). Preferably, the radical initiator with a long half-life time will have a half-life time of 6 to 15 hrs., preferably 8 to 10 hrs. Suitable radical intiators with a long half-life time include alkyl (substituted or not, linear or branched) aryl (unsubstituted or substituted up to five substituents) or acyl peroxides, alkyl and aryl hydroperoxides, alkyl and aryl peresters, the most preferred (but not limited to) initiators being dicumyl peroxide, di-t-butyl peroxide, di-t-amyl peroxide, t-butyl hydroperoxide. Generally, these radical initiators are added to the polymerization reaction in amounts of about 1–40 mol %, preferably 5–20 mol % based on the total concentration of nitroxyl radical (II) and alkoxyamine used (I). Preferably, these radical initiators are added at the beginning of the polymerization reaction, although the radical initiators may be added portion-wise during the course of polymerization if desired.

Nitroxyl radical-mediated polymerization may be conducted substantially as described in U.S. Pat. No. 4,581,429 with the additional use of the long half-life radical initiator according to the present invention. U.S. Pat. No. 4,581,429 is incorporated herein by reference in its entirety.

Suitable groups for X in formula (I) are alkyl and aryl, preferably tertiary butyl, cyanoisopropyl, benzyl, 1-phenylethyl, indenyl or the like. In general the structure of X. will be of the form

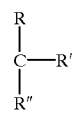

wherein R, R' and R", are the same or different and may be selected from hydrogen, alkyl, phenyl, cyano, carboxcylic acid, or carboxylic groups including substituted groups thereof.

Suitable groups for $R^1$, $R^2$, $R^5$ and $R^6$ are straight or branched alkyl groups of $C_1$–$C_{20}$; preferably $C_1$–$C_{10}$ such as methyl, ethyl, propyl, butyl, isopropyl, isobutyl, t-butyl, neo-pentyl, $C_6$–$C_{30}$ aromatic and substituted aromatic groups such as benzyl, aryl(phenyl) or the like, $C_1$–$C_{30}$, preferably $C_4$–$C_7$ cyclic alkyl groups, etc.

Suitable groups for $R^3$ and/or $R^4$ are as above for $R^1$, $R^2$, $R^5$ and $R^6$ and include methyl, ethyl, propyl, butyl, iospropyl, isobutyl, t-butyl, pentyl, octadecyl or the like, or if $R^3CNCR^4$ is part of a cyclic structure this cyclic structure may be

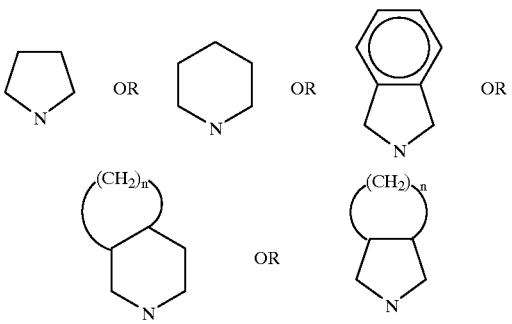

The cyclic structure may be substituted.

For controlled free radical polymerization by the initiators of formula I it is preferable that the nitroxide radical of formula II does not initiate any substantial free radical polymerization of the unsaturated monomers itself.

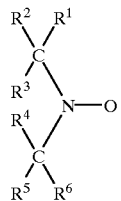
(II)

where $R^1$–$R^6$ are as above for formula (I).

Hindered alkoxy amines generally in accordance with the present invention can be used as initiators of free radical polymerization at convenient temperatures. The polymerization processes proceed by "insertion" of monomer units between the nitroxide radical of the formula II and X. via radical intermediates, for example

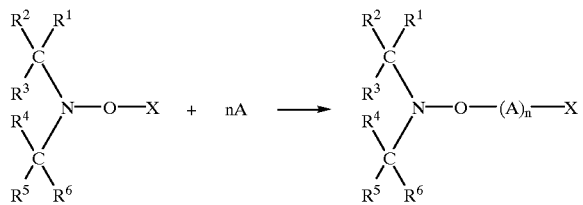

Alkoxy amines such as those of formula I can be prepared by heating a nitroxide radical of formula II in the presence of a stoichiometric amount of a carbon centered free radical X. where X. may be generated by any of the methods well known in the art, e.g. by the decomposition of an azo compound, by Scission of an alkoxy radical or by H atom abstraction from a suitable monomeric or polymeric compound or by addition of a free radical to an olefin. More specifically X. can be generated by the thermal or photochemical dissociation of X—X, or X—Z—X or X—Z—Z—X, where Z is a group which in its uncombined form is a small stable molecule e.g., $CO_2$ or $N_2$.

The alkoxyamine so formed may be isolated and purified for later use or it may be used without further purification for the initiation of polymerization.

The nitroxides of formula II may be readily prepared by the oxidation of the appropriate secondary amine or hydroxylamine, reduction of the appropriate nitro or nitroso compound, or by the addition of free radicals to nitrones.

Alternatively the alkoxyamine initiators can either be prepared or generated in situ by the addition of a source of the free radicals to a suitable nitroxyl radical in the presence of an unsaturated monomer or with the monomer being added after the free radicals have reacted with the nitroxide. The free radicals can be generated by any of the methods well known in the art, e.g. by the decomposition of an azo compound, by scission of an alkoxy radical or by H atom abstraction from a suitable monomeric or polymeric compound, or by addition of a free radical to an olefin.

Preferably in the method of the present invention, the polymerization is performed in a non-polymerizable medium such as for example benzene, toluene, xylene, dimethoxybenzene, diglyme, diphenyl ether or the like.

The method of this invention is particularly suitable for the production of oligomeric polymers and copolymers including block and graft copolymers, and of course includes the reaction of two or more different monomers.

It is thus possible to control the polymerization processes of the present invention by selecting alkoxyamines of formula I with appropriate substituents, selecting the polymerization temperature, and the amount and type of monomer(s) added at any one time as well as the amount and type of the secondary radical initiator. Additional nitroxide radical of formula II may be added if desired, such as for example to stabilize growing polymer chain. Although this controlled growth radical polymerization will proceed until the monomer present is consumed and then stop, the polymeric free radical is in effect "living" and polymerization will continue if further amounts of a polymerizable monomer are added. This additional monomer may not necessarily be the same as the previous monomer hence this controlled growth free radical polymerization has some advantages such as for example the flexibility and ability to produce polymers of controlled chain length and to produce block and graft copolymers. Further, the present method is applicable to a wide range of monomers. Additionally, it is now possible to readily prepared short chain oligomeric polymers from unsaturated monomers because the polymer chain length in any one polymerization step can be controlled by the relative amounts of monomer and initiator present in the reaction.

In the present invention any radically polymerizable alkene can serve as a monomer for polymerization. The preferred monomers include those of the formula:

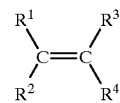

wherein $R^1$ and $R^2$ are independently selected from the group consisting of H, halogen, $CF_3$, straight or branched alkyl of 1 to 20 carbon atoms (preferably from 1 to 6 carbon atoms, more preferably from 1 to 4 carbon atoms), aryl, α,β-unsaturated straight or branched alkenyl or alkynyl of 2 to 10 carbon atoms (preferably from 2 to 6 carbon atoms, more preferably from 2 to 4 carbon atoms), α,β-unsaturated straight or branched alkenyl of 2 to 6 carbon atoms (preferably vinyl) substituted (preferably at the α-position) with a halogen (preferably chlorine), $C_3$–$C_8$ cycloalkyl, hetercyclyl, $C(=Y)R^5$, $C(=Y)NR^6R^7$ and $YC(=Y)R^8$, where Y may be $NR^8$ or O (preferably O), $R^5$ is alkyl of from 1 to 20 carbon atoms, alkoxy of from 1 to 20 carbon atoms, aryloxy or heterocyclyloxy, $R^6$ and $R^7$ are independently H or alkyl of from 1 to 20 carbon atoms, or $R^6$ and $R^7$ may be joined together to form an alkylene group of from 2 to 5 carbon atoms, thus forming a 3- to 6-membered ring, and $R^8$ is H, straight or branched $C_1$–$C_{20}$ alkyl and aryl; and $R^3$ is selected from the group consisting of H, halogen (preferably fluorine or chlorine), $C_1$–$C_6$ (preferably $C_1$) alkyl, $COOR^9$ (where $R^9$ is H, an alkali metal, or a $C_1$–$C_6$ alkyl group) or aryl, or amid $R^{10,11}{}_2N$—, where $R^{10,11}$ is H, alkyl, aryl; or $R^1$ and $R^3$ may be joined to form a group of the formula $(CH_2)_{n'}$ (which may be substituted with from 1 to 2n' halogen atoms or $C_1$–$C_4$ alkyl groups) or C(=O)—Y—C(=O), where n' is from 2 to 6 (preferably 3 or 4) and Y is as defined above; or $R^4$ is the same as $R^1$ or $R^2$ or optionally $R^4$ is a CN group;

at least two of $R^1$, $R^2$, and $R^3$ are H or halogen.

In the context of the present application, the terms "alkyl", "alkenyl" and "alkynyl" refer to straight-chain or branched groups (except for $C_1$ and $C_2$ groups).

Furthermore, in the present application, "aryl" refers to phenyl, naphthyl, phenanthryl, phenalenyl, anthracenyl, triphenylenyl, fluoranthenyl, pyrenyl, pentacenyl, chrysenyl, naphthacenyl, hexaphenyl, picenyl and perylenyl (preferably phenyl and naphthyl), in which each hydrogen atom may be replaced with alkyl of from 1 to 20 carbon atoms (preferably from 1 to 6 carbon atoms and more preferably methyl), alkyl of from 1 to 20 carbon atoms (preferably from 1 to 6 carbon atoms and more preferably methyl) in which each of the hydrogen atoms is independently replaced by a halide (preferably a fluoride or a chloride), alkenyl of from 2 to 20 carbon atoms, alkynyl of from 1 to 20 carbon atoms, alkoxy of from 1 to 6 carbon atoms, alkylthio of from 1 to 6 carbon atoms, $C_3$–$C_8$ cycloalkyl, phenyl, halogen, $NH_2$, $C_1$–$C_6$-alkylamino, $C_1$–$C_6$-dialkylamino, and phenyl which may be substituted with from 1 to 5 halogen atoms and/or $C_1$–$C_4$ alkyl groups. (This definition of "aryl" also applies to the aryl groups in "aryloxy" and "aralkyl.") Thus, phenyl may be substituted from 1 to 5 times and naphthyl may be substituted from 1 to 7 times (preferably, any aryl group, if substituted, is substituted from 1 to 3 times) with one of the above substituents. More preferably, "aryl" refers to phenyl, naphthyl, phenyl substituted from 1 to 5 times with fluorine or chlorine, and phenyl substituted from 1 to 3 times with a substituent selected from the group consisting of alkyl of from 1 to 6 carbon atoms, alkoxy of from 1 to 4 carbon atoms and phenyl. Most preferably, "aryl" refers to phenyl and tolyl.

In the context of the present invention, "heterocyclyl" refers to pyridyl, furyl, pyrrolyl, thienyl, imidazolyl, pyrazolyl, pyrazinyl, pyrimidinyl, pyridazinyl, pyranyl, indolyl, isoindolyl, indazolyl, benzofuryl, isobenzofuryl, benzothienyl, isobenzothienyl, chromenyl, xanthenyl, purinyl, pteridinyl, quinolyl, isoquinolyl, phthalazinyl, quinazolinyl, quinoxalinyl, naphthyridinyl, phenoxathiinyl, carbazolyl, cinnolinyl, phenanthridinyl, acridinyl, 1,10-phenanthrolinyl, phenazinyl, phenoxazinyl, phenothiazinyl, oxazolyl, thiazolyl, isoxazolyl, isothiazolyl, and hydrogenated forms thereof known to those in the art. Preferred heterocyclyl groups include pyridyl, furyl, pyrrolyl, thienyl, imidazolyl, pyrazolyl, pyrazinyl, pyrimidinyl, pyridazinyl, pyranyl and indolyl, the most preferred heterocyclyl group being pyridyl. Accordingly, suitable vinyl heterocycles to be used as a monomer in the present invention include 2-vinyl pyridine, 4-vinyl pyridine, 2-vinyl pyrrole, 3-vinyl pyrrole, 2-vinyl oxazole, 4-vinyl oxazole, 5-vinyl oxazole, 2-vinyl thiazole, 4-vinyl thiazole, 5-vinyl thiazole, 2-vinyl imidazole, 4-vinyl imidazole, 3-vinyl pyrazole, 4-vinyl pyrazole, 3-vinyl pyridazine, 4-vinyl pyridazine, 3-vinyl isoxazole, 3-vinyl isothiazoles, 2-vinyl pyrimidine, 4-vinyl pyrimidine, 5-vinyl pyrimidine, any vinyl pyrazine, N-vinyl carbazole, N-vinyl pyrrolidone, N-vinyl imidazole, the most preferred being 2-vinyl pyridine and N-vinyl imidazole. The vinyl heterocycles mentioned above may bear one or more (preferably 1 or 2) $C_1$–$C_6$ alkyl or alkoxy groups, cyano groups, ester groups or halogen atoms, either on the vinyl group or the heterocyclyl group, but preferably on the heterocyclyl group. Further, those vinyl heterocycles which, when unsubstituted, contain an N-H group may be protected at that position with a conventional blocking or protecting group, such as a $C_1$–$C_6$ alkyl group, a tris-$C_1$–$C_6$ alkylsilyl group, an acyl group of the formula $R^{12}CO$ (where $R^{12}$ is alkyl of from 1 to 20 carbon atoms, in which each of the hydrogen atoms may be independently replaced by halide, preferably fluoride or chloride), alkenyl of from 2 to 20 carbon atoms (preferably vinyl), alkynyl of from 2 to 10 carbon atoms (preferably acetylenyl), phenyl which may be substituted with from 1 to 5 halogen atoms or alkyl groups of from 1 to 4 carbon atoms, or aralkyl (aryl-substituted alkyl, in which the aryl group is phenyl or substituted phenyl and the alkyl group is from 1 to 6 carbon atoms), etc. (This definition of "heterocyclyl" also applies to the heterocyclyl groups in "heterocyclyloxy" and "heterocyclic ring.")

More specifically, preferred monomers include (but not limited to) styrene, p-chloromethylstyrene, vinyl chloroacetate, acrylate and methacrylate esters of $C_1$–$C_{20}$ alcohols, vinyl acetate, 2-vinyl pyridine, 2-vinyl imidazole, butadiene, 2-(2-bromopropionoxy) ethyl acrylate, acrylonitrile, and methacrylonitrile.

A monomer containing at least one polar group may be present in an amount of 0 to 100 wt % by weight based on the total amount of monomers. A preferred amount of the monomer containing at least one polar group is 10 to 100 wt %; the most preferred amount is 20 to 80 wt % based on the total amount of monomers. This is particularly important in the case of acrylonitrile because an amount of at least 20 wt % assures solvent resistance properties of the resulting polymer.

The polymers prepared by the process of the present invention may be oligomers which have functional groups capable of undergoing further chemical reactions to form useful materials. The polymers produced by the methods of the present invention will have a terminal oxyamine group such as that shown as formula II on one end of the chain and an initiator residue (X) on the other end and depending upon the monomers used may have chemically reactive functional groups along the chain. Thus the products of this method will have at least one functional group per molecule. If the last monomer unit is α-alkyl (methyl, ethyl) substituted, the oxyamine can decompose to form the unsaturated terminal group

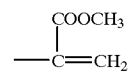

and a hydroxylamine; these oligomeric polymers with terminal unsaturation have been named macromers. Macromers are capable of further polymerization or copolymerization via the unsaturated group to give a polymer with pendent chains.

The alkoxyamines may have other functional groups which can be used for further reactions of the oligomers if the nitroxide end group can be kept as part of the polymer molecule. Alternatively the group X derived from the initial free radical initiator may contain functional groups.

A mixture of monomers can be added in the polymerization step to produce a random copolymer similar to that produced by normal free radical polymerization except with controlled chain length.

If necessary the block copolymers can be provided with reactive functional groups as described above.

Polymers which are produced by the present invention generally have a polydispersity less than or equal to 1.50, more preferably between 1.1 and 1.4, and even more preferably between 1.1 and 1.3. The polymers generally have a molecular weight ($M_n$) of about 3,000–150,000, preferably 10,000–50,000.

In one embodiment of the process of the present invention there is provided a two stage method for preparing a graft copolymer by forming in a first stage reaction a polymer with pendent alkoxyamine groups of the general structure of formula I, and adding further monomer to the product of the first stage reaction to form a graft copolymer by controlled growth free radical polymerization. The graft copolymer may be isolated in ways well known in the art. It should be noted that this method gives graft copolymer substantially free from any homopolymer. One method of making a polymer with alkoxyamine groups is by creating free radical sites on a preformed polymer in the presence of a nitroxide. This may be achieved by the methods described above or by reacting the polymer with a free radical which is capable of abstracting a hydrogen atom from the polymer in the presence of the nitroxide. Preferred free radicals for this are oxygen centered radicals such as hydroxy, t-butoxy and benzoyloxy. Optionally the product of this reaction may be isolated, for analysis and storage, or the next stage of the reaction may be carried out without isolation. In another embodiment of the processes of the present invention there is provided a method of making a polymer with alkoxyamine groups by copolymerizing two or more monomers wherein at least one of the monomers contains an alkoxyamine group so as to be capable of forming the polymer containing alkoxyamine groups of the structure of formula I.

The alkoxyamine can be any of those specified in formula I. The grafted chains can be formed by any of the polymerization processes described herein and may themselves by homopolymers, random copolymers or block copolymers.

The process of the invention can also be successfully applied to modify the procedure of Georges at al[18] in which a reaction mixture containing the monomer, initiator (BPO) and excess compound of formula (I) (TEMPO; for example, 1.3 times with respect to the concentration of BPO) is first thermostated at 95° C. for 3.5 hrs. in order to produce the corresponding alkoxyamine (from BPO and TEMPO), and subsequently heated to 120° C. at which temperature the polymerization begins. This procedure yields polymers with the most narrow molecular weights distributions ($M_w/M_n \approx 1.10$). In the modified procedure the rate enhancement is achieved by using a mixed initiator (BPO+20–30 mol % dicumyl peroxide. The reaction is approximately 2–3 times faster than in the absence of dicumyl peroxide. At the same time, the resulting polymers retain narrow polydispersities ($M_w/M_n \approx 1.25$).

FIG. 1 shows kinetic plots for polymerization of TEMPO initiated by 1-phenylethyl-TEMPO adduct in the presence of a variable amount of dicumyl peroxide. The rate of polymerization increases with the increase of the amount of dicumyl peroxide (DCP) added. The plots are linear indicating a steady state for propagating radicals within the conversions studied. The slopes of the plots of $\ln([M]_o/[M])$ vs. time become larger for higher dicumyl peroxide content which suggests an increase of the stationary concentration of the growing radicals.

Figure 2:
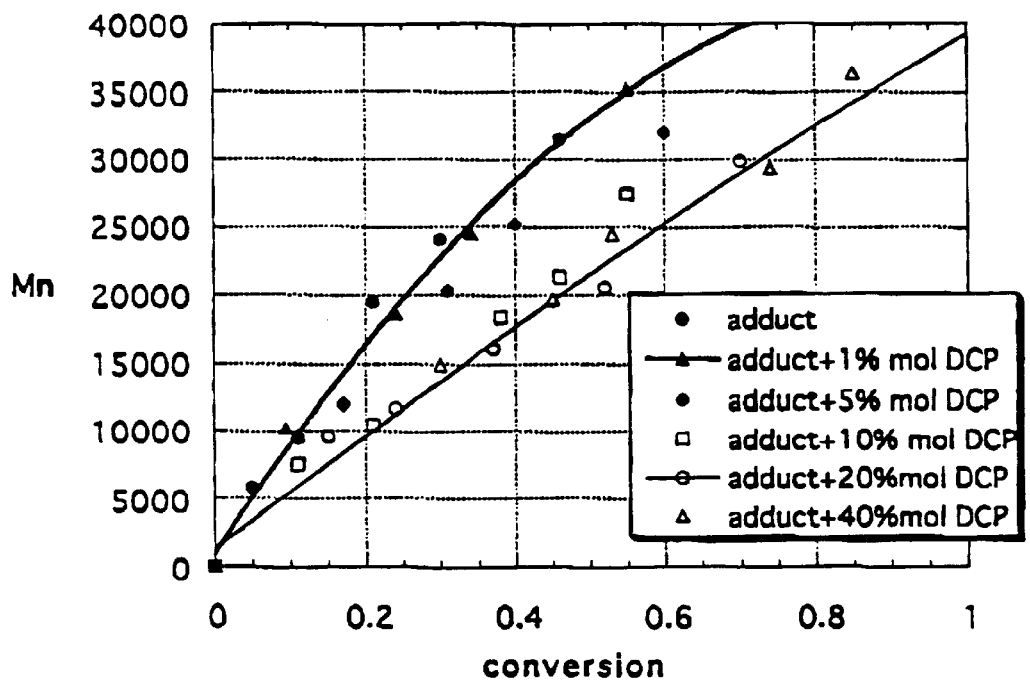
FIG. 2 shows evolution of molecular weights with conversion for a bulk polymerization of styrene in the presence of 1-phenylethyl-TEMPO adduct (0.010M) and variable amounts of dicumyl peroxide; temperature 120° C.

The molecular weights of the resulting polymers decrease with an increasing amount of dicumyl peroxide added (FIG. 2). The radicals introduced by decomposition of the initiator react with TEMPO increasing the total number of chains. However the decrease of molecular weights is significant only at higher concentrations of dicumyl peroxide (10–40% mol). FIG. 2 also shows that for the polymerizations with higher initial content of dicumyl peroxide the plots of molecular weights vs. conversion are linear even at high conversion (>80%), in contrast to a polymerization in the presence of the adduct alone, where the plots of molecular weights vs. conversion show a tendency to level off at high conversions.

Figure 3:
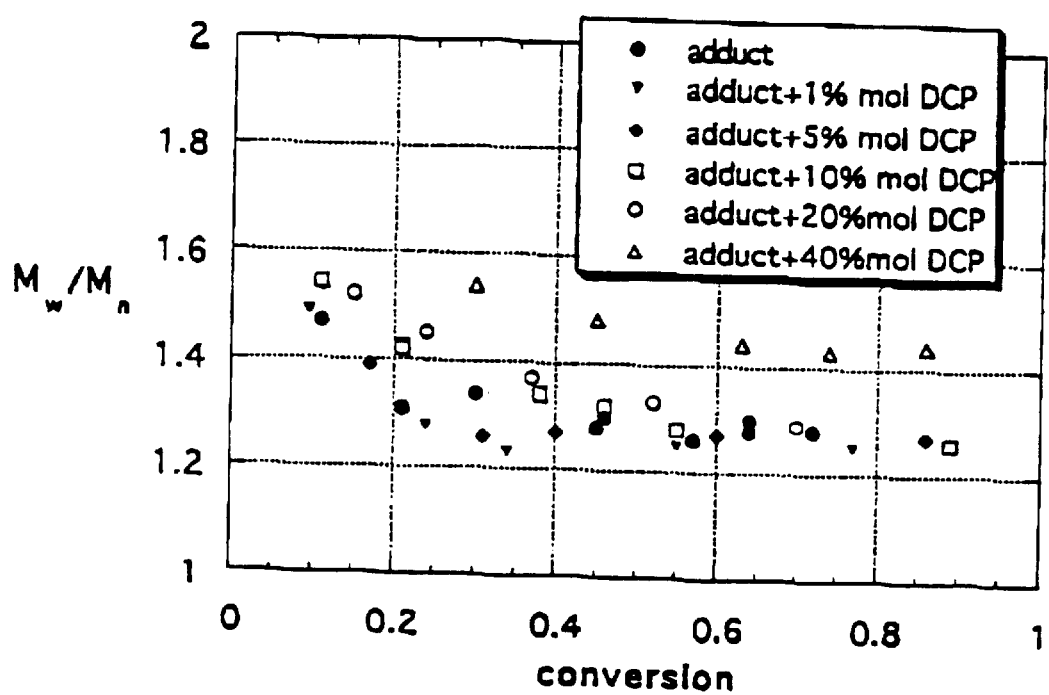
FIG. 3 shows the dependence of molecular weights distribution upon conversion for a bulk polymerization of styrene in the presence of 1-phenylethyl-TEMPO adduct (0.010M) and variable amounts of dicumyl peroxide, temperature 120° C.

Introducing an additional source of radicals in the form of a radical initiator to the TEMPO-mediated polymerization of styrene leads to a broadening of polydispersities of the resulting polymers. Indeed, when dicumyl peroxide is added to a polymerization of styrene initiated by 1-phenylethyl—TEMPO adduct, a broadening of polydispersities is observed (FIG. 3), but it is noticeable only at the highest content of dicumyl peroxide ($M_w/M_n=1.45$ at 40 mol %) and even then it is lower then the limiting polydispersity for a conventional radical polymerization $M_w/M_n=1.5$. At moderate content of the radical initiator the polydispersities are as low as in the presence of the adduct only.

Figure 4:
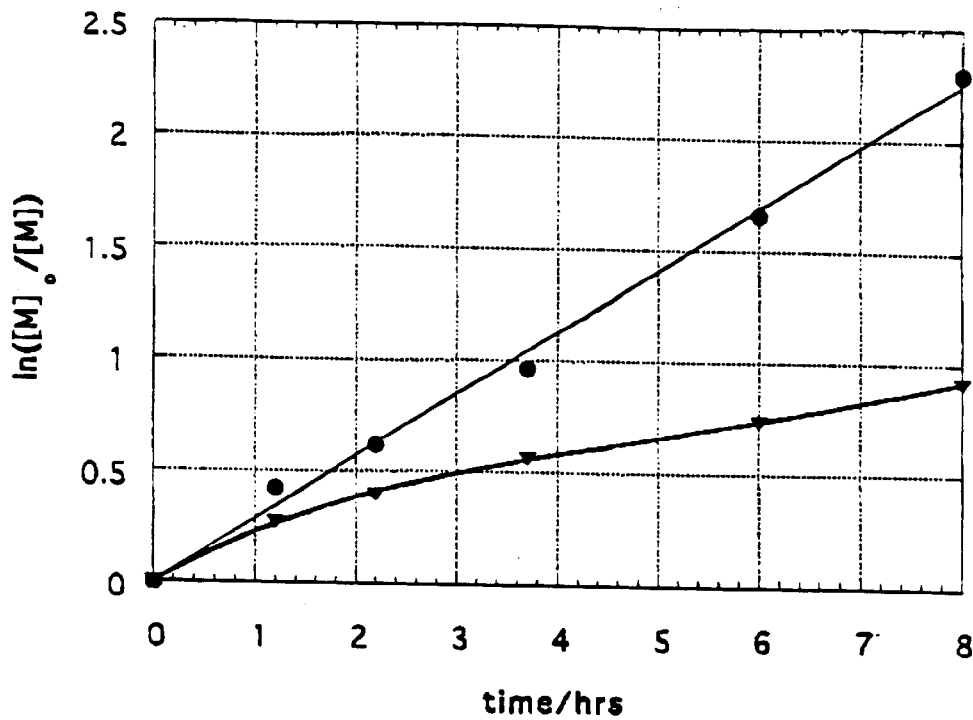
FIG. 4 shows kinetic plots of $\ln([M]_o/[M])$ vs. time for bulk polymerization of styrene initiated by AIBN (0.01M) in the presence of TEMPO (0.01M) w/o dicumyl peroxide (▼) and with 20 mol % of dicumyl peroxide (●); temperature 120° C.
Figure 5:
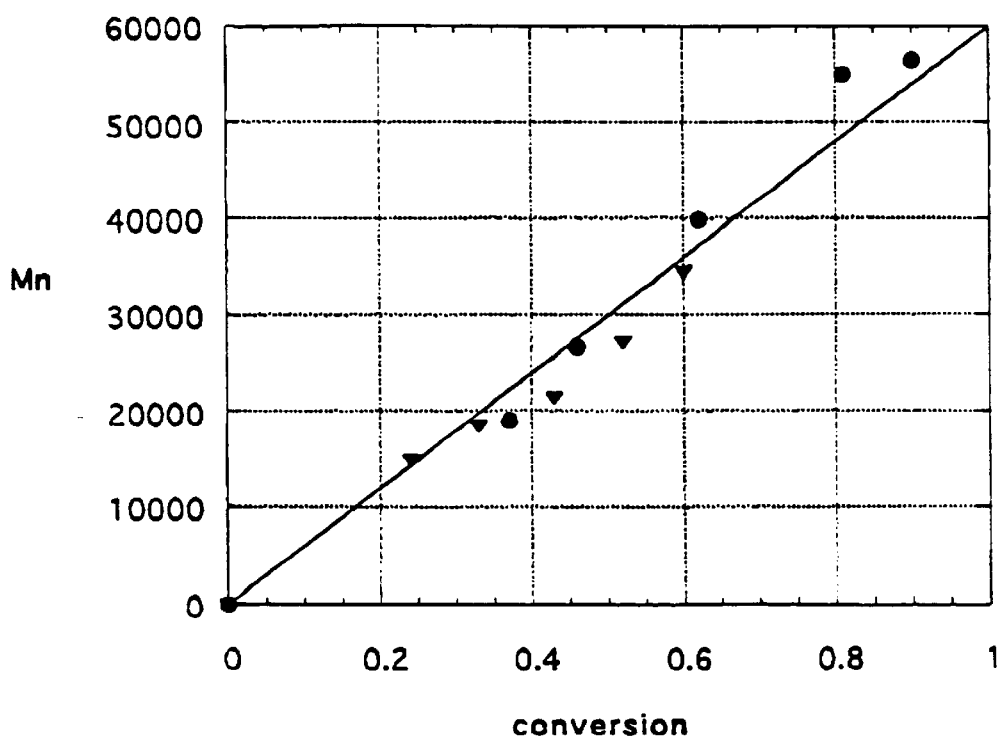
FIG. 5 shows the evolution of molecular weights with conversion for bulk polymerization of styrene initiated by AIBN (0.01M) in the presence of TEMPO (0.01M) w/o dicumyl peroxide (▼) and with 20 mol % of dicumyl peroxide (●); temperature 120° C.

A similar approach to a rate enhancement (e.g. by addition of a long half-life radical initiator) is useful for polymerization of a monomer (styrene) initiated by a second initiator such as azo-iso-butyronitrile (AIBN) or benzoyl peroxide (BPO) in the presence of TEMPO. The polymerization procedure and polymer characterizations are generally identical to that for the polymerizations in the presence 1-phenylethyl-TEMPO adduct. In this system the effect of addition of dicumyl peroxide has even more pronounced effect on the polymerization relative to for the previously described system (FIG. 4). The molecular weights increase linearly with conversion (FIG. 5) indicating that the polymerization proceeds in a controlled manner.

A primary initiator is a radical initiator used in a stoichimetric or substoichimetric amount based on the nitroxyl radical having a half-life time less than 10 min, at the polymerization temperature. A secondary initiator is a radical initiator with a long half-life time (preferrably 8–10 hrs) at the polymerization temperature.

Other features of the invention will become apparent in the course of the following descriptions of exemplary embodiments which are given for illustration of the invention and are not intended to be limiting thereof.

EXAMPLES

Materials

Styrene (Aldrich) was dried over $CaH_2$ and distilled under vacuum prior to the polymerization. The initiators, AIBN (Eastman-Kodak) and BPO (Aldrich) were purified by recrystallization from methanol. Dicumyl peroxide (Aldrich, 98% pure) was used as received. The 1-phenylethyl-TEMPO adduct was synthesized as described below.

Polymerizations

A series of polymerizations of styrene in the presence of 1-phenylethyl-TEMPO adduct with variable amount of dicumyl peroxide were performed. A typical polymerization procedure was as follows: monomer, adduct or initiator (AIBN or BPO) and TEMPO and dicumyl peroxide (a stock solution in styrene) were added to a Schlenk flask under argon and the reaction mixture was thermostated in an oil-bath at 120° C. Samples were taken from the reaction mixture after variable times. The monomer conversion was determined gravimetrically. The molecular weights measurements by gel permeation chromatography (GPC) were performed on the samples from the reaction mixture after diluting with tetrahydrofuran (THF).

The modified procedure was carried out as follows: the monomer and TEMPO, and mixed initiators (BPO+20–30 mol % of dicumyl peroxide based on the amount of TEMPO) were added under argon to a Schlenk flask and thermostated for 3–3.5 hrs. and then heated to 120° C. The monomer conversion and molecular weights were determined as described above.

Example 1

Polymerization of Styrene Initiated by 1-Phenylethyl-TEMPO Adduct and Dicumyl Peroxide.

a) 1 mol % of Dicumyl Peroxide (With Respect to the Adduct)

A stock solution of dicumyl peroxide (0.0267 g) in styrene (5 ml) was prepared under argon. 0.0260 g ($1 \cdot 10^{-4}$ mole) of the adduct, 0.050 ml of the stock solution of dicumyl peroxide and 9.950 ml of styrene were added under argon to a Schlenk flask equipped with a magnetic stirrer. The reaction mixture was heated in an oil-bath to 120° C. After variable reaction times, samples were withdrawn from the reaction mixture and evaluated by GPC. The conversions were determined gravimetrically by evaporation of the unreacted monomer. The final polymer obtained after 21 hrs. (77% conversion) had $M_n$=48,000 and molecular weight distribution $M_w/M_n$=1.22.

b) 5 mol % of Dicumyl Peroxide (With Respect to the Adduct)

A stock solution of dicumyl peroxide (0.0267 g) in styrene (5 ml) was prepared under argon. 0.0260 g ($1 \cdot 10^{-4}$ mole) of the adduct, 0.250 ml of the stock solution of dicumyl peroxide and 9.750 ml of styrene were added under argon to a Schlenk flask equipped with a magnetic stirrer. The reaction mixture was heated in an oil-bath to 120° C. After variable reaction times, samples were withdrawn from the reaction mixture and evaluated by GPC. The conversions were determined gravimetrically by evaporation of the unreacted monomer. The final polymer obtained after 21 hrs. (86% conversion) had $M_n$=51,000 and molecular weight distribution $M_w/M_n$=1.27.

c) 10 mol % of Dicumyl Peroxide (With Respect to the Adduct)

A stock solution of dicumyl peroxide (0.0231 g) in styrene (5 ml) was prepared under argon. 0.0130 g ($5 \cdot 10^{-5}$ mole) of the adduct, 0.282 ml of the stock solution of dicumyl peroxide and 4.718 ml of styrene were added under argon to a Schlenk flask equipped with a magnetic stirrer. The reaction mixture was heated in an oil-bath to 120° C. After variable reaction times, samples were withdrawn from the reaction mixture, diluted with THF and evaluated by GPC. The conversions were determined gravimetrically by evaporation of the unreacted monomer. The final polymer obtained after 22.5 hrs. (89% conversion) had $M_n$=36,000 and molecular weight distribution $M_w/M_n$=1.26.

d) 20 mol % of Dicumyl Peroxide (With Respect to the Adduct)

A stock solution of dicumyl peroxide (0.0187 g) in styrene (5 ml) was prepared under argon. 0.0130 g ($5 \cdot 10^{-5}$ mole) of the adduct, 0.722 ml of the stock solution of dicumyl peroxide and 4.278 ml of styrene were added under argon to a Schlenk flask equipped with a magnetic stirrer. The reaction mixture was heated in an oil-bath to 120° C. After variable reaction times, samples were withdrawn from the reaction mixture and evaluated by GPC. The conversions were determined gravimetrically by evaporation of the unreacted monomer. The final polymer obtained after 8.3 hrs. (70% conversion) had $M_n$=30,000 and molecular weight distribution $M_w/M_n$=1.29.

e) 40 mol % of Dicumyl Peroxide (With Respect to the Adduct)

A stock solution of dicumyl peroxide (0.0458 g) in styrene (5 ml) was prepared under argon. 0.0130 g ($5 \cdot 10^{-5}$ mole) of the adduct, 0.586 ml of the stock solution of dicumyl peroxide and 4.414 ml of styrene were added under argon to a Schlenk flask equipped with a magnetic stirrer. The reaction mixture was heated in an oil-bath to 120° C. After variable reaction times, samples were withdrawn from the reaction mixture and evaluated by GPC. The conversions were determined gravimetrically by evaporation of the unreacted monomer. The final polymer obtained after 7.5 hrs. (86% conversion) had $M_n$=37,000 and molecular weight distribution $M_w/M_n$=1.44.

Example 2

Polymerization of Styrene Initiated by AIBN/TEMPO 1:1 and Dicumyl Peroxide (20 mol % With Respect to AIBN)

A stock solution of dicumyl peroxide (0.0272 g) in styrene (5 ml) was prepared under argon. 0.0164 g ($1 \cdot 10^{-4}$ mole) of AIBN, 0.0156 g ($1 \cdot 10^{-4}$ mole) of TEMPO, 0.993 ml of the stock solution of dicumyl peroxide and 9.007 ml of styrene were added under argon to a Schlenk flask equipped with a magnetic stirrer. The reaction mixture was heated in an oil-bath to 120° C. After variable reaction times, samples were withdrawn from the reaction mixture and evaluated by GPC. The conversions were determined gravimetrically by evaporation of the unreacted monomer. The final polymer obtained after 8 hrs. (90% conversion) had $M_n$=56,500 and molecular weight distribution $M_w/M_n$=1.55.

Example 3

Polymerization of Styrene Initiated by BPO/TEMPO 1:1 and Dicumyl Peroxide (20 mol % With Respect to BPO)

0.0242 g ($1 \cdot 10^{-4}$ mole) of BPO, 0.0172 g ($1 \cdot 10^{-4}$ mole) of TEMPO, 0.0055 g ($2 \cdot 10^{-5}$ mole) of dicumyl peroxide and 10 ml of styrene were added under argon to a Schlenk flask equipped with a magnetic stirrer. The reaction mixture was heated in an oil-bath to 120° C. After variable reaction times, samples were withdrawn from the reaction mixture and evaluated by GPC. The conversions were determined gravimetrically by evaporation of the unreacted monomer. The final polymer obtained after 8 hrs. (50% conversion) had $M_n$=36,000 and molecular weight distribution $M_w/M_n$=1.45.

Example 4

Modified Polymerization of Styrene Initiated by BPO/TEMPO 1:1.1 and Dicumyl Peroxide (35 mol % With Respect to BPO)

0.0262 g ($1.1 \cdot 10^{-4}$ mole) of BPO, 0.0189 g ($1.2 \cdot 10^{-4}$ mole) of TEMPO, 0.0107 g ($3.9 \cdot 10^{-5}$ mole) of dicumyl peroxide and 10 ml of styrene were added under argon to a Schlenk flask equipped with a magnetic stirrer. The reaction mixture was heated in an oil-bath to 90° C. for 3 hrs. and then the temperature was increased to 120° C. After variable reaction times, samples were withdrawn from the reaction mixture and evaluated by GPC.

The conversions were determined gravimetrically by evaporation of the unreacted monomer. The final polymer obtained after 6 hrs. (88% conversion) had $M_n$=53,000 and molecular weight distribution $M_w/M_n$=1.38.

Example 5

Modified Polymerization of Styrene Initiated by BPO/TEMPO 1:1.3 and Dicumyl Peroxide (20 mol % With Respect to BPO)

0.0242 g ($1 \cdot 10^{-4}$ mole) of BPO, 0.0203 g ($1.3 \cdot 10^{-4}$ mole) of TEMPO, 0.0054 g ($2.5 \cdot 10^{-5}$ mole) of dicumyl peroxide and 10 ml of styrene were added under argon to a Schlenk flask equipped with a magnetic stirrer. The reaction mixture was heated in an oil-bath to 90° C. for 3.5 hrs. and then the temperature was increased to 120° C. After variable reaction times, samples were withdrawn from the reaction mixture and evaluated by GPC. The conversions were determined gravimetrically by evaporation of the unreacted monomer. The final polymer obtained after 9.5 hrs. (72% conversion) had $M_n$=48,000 and molecular weight distribution $M_w/M_n$= 1.24.

Example 6

Synthesis of 1-phenylethyl-TEMPO Adduct (2,2,6,6-Tetramethyl-1-(1-phenylethoxy)piperidine 2,2,6,6-Tetramethyl-1-(1-phenylethoxy)piperidine was synthesized in 90% yield at 20° C. via entrapment by TEMPO of the 1-phenylethyl radical produced from 1-phenylethyl bromide (1 mol. equivalent), CuBr (1 mol. equivalent) and 2,2'-bispyridine (2 mol. equivalents) in benzene. The adduct was purified by column chromatography and recrystallization from cold ethanol and its purity as determined by NMR and EPR was >99%.

In this invention, a rate enhancement of nitroxyl radical-mediated polymerization of monomers is achieved by addition of a small amount of a radical initiator with a long half-life time at the polymerization temperature. For example, the polymerization of styrene with dicumyl peroxide added in the amount up to 40 mol % proceeds with a higher rate than analogous polymerization in the absence of the radical initiator. At the same time, molecular weights increase linearly with conversion and are only slightly lower than expected when less than 40 mol % of the initiator is added. Also, the polydispersities remain narrow and close to those obtained in the systems without an additional initiator.

REFERENCES

1) Solomon, D. H.; Waverly, G.; Rizzardo, E.; Hill, W.; Cacioli, P. U.S. Pat. No. 4,581,429.
2) Georges, M. K.; Veregin, R. P. N.; Kazmaier, P. M.; Hamer, G. K. *Macromolecules* 1993, 26, 2987.
3) Mardare, D.; Matyjaszewski, K. *ACS Polymer Preprints* 1994 35(1), 778.
4) Hawker, C. J. *J. Am. Chem. Soc.* 1994, 116, 11185.
5) Li, I.; Howell, B. A.; Ellaboudy, A.; Kastl, P. E.; Priddy, D. B. *ASC Polym. Preprints* 1995, 36(1), 469.
6) Catala, J. M.; Bubel, F.; Hammouch, S. O *Macromolecules* 1995, 28, 8441.
7) Puts, R. D.; Sogah, D. Y. *Macromolecules* 1996, 29, 3323.
8) Hawker, C. J.; Elce, E.; Dao, J.; Volksen, W.; Russel, T. P.; Barclay, G. G. *Macromolecules* 1996, 29, 2686.
9) Fukuda, T.; Terauchi, T.; Goto, A.; Tsujii, Y.; Miyamoto, T. *Macromolecules,* 1996, 29, 3050.
11) Fukuda, T.; Terauchi, T. *Chem. Letters,* 1996, 4, 293.
11b) Greszta, D., Matyjaszewski, K., *Macromolecules,* 1996, 29, 5239.
11c) Greszta, D., Matyjaszewski, K., Priddy, D. B., Li, I., Howell, B. A.,*ACS Polymer Preprints,* 1996, 37(2), 519.
12) Veregin, R. P. N.; Odell, P. G.; Michalak, L. M.; Georges, M. K. *Macromolecules* 1996, 29, 2746.
14) Fisher, H. *J. Am. Chem. Soc.* 1986, 108, 3925.
15) Georges, M. K.; Veregin, R. P. N.; Kazmaier, P. M.; Hamer, G. K.; Saban. M. *Macromolecules* 1994, 27, 7228.
16) Odell, P. G.; Veregin, R. P. N.; Michalak, L. M.; Brousmiche, D.; Georges, M. K. *Macromolecules* 1995, 28, 8453.
17) Veregin, R. P. N.; Odell, P. G.; Michalak, L. M.; Georges, M. K. *Macromolecules* 1996, 29, 4161.
18) Georges, M. K.; Veregin, R. P. N.; Kazmaier, P. M.; Hamer, G. K. *Macromolecules* 1993, 26, 5316.

These references are incorporated herein by reference in their entirety.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the Unites States is:

1. A method for the production of a (co)polymer by free radical polymerization of an unsaturated monomer, comprising:
heating the unsaturated monomer in the presence of:
a compound according to the formula (I)

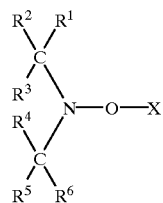

(I)

at a polymerization temperature, wherein the polymerization temperature is sufficient to dissociate the compound according to formula (I) into a free radical polymerization initiating radical X., and a stable free radical of formula (II),

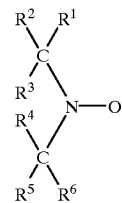

(II)

wherein X represents a group having at least one carbon atom and is capable of polymerizing the unsaturated monomer by free radical polymerization, $R^1$, $R^2$, $R^5$ and $R^6$ are the same or different straight chain or branched substituted or unsubstituted alkyl groups of a chain length sufficient to provide steric hindrance and weakening of the O—X bond of the compound of formula I, and $R^3$ and $R^4$ represent the same or different straight chain or branched substituted alkyl groups or $R^3CNCR^4$ may be part of a cyclic or heterocyclic structure which may have fused with it another saturated or aromatic ring, the cyclic structure or aromatic ring being optionally substituted and,
a compound selected from a group consisting of radicals or compounds that may form radicals at the polymerization temperature that can react with, or complex, the stable free radical of formula (II) to thereby maintain a substantially constant polymerization rate throughout the polymerization process.

2. The method of claim 1, wherein the (co)polymer being formed is a graft copolymer, and wherein one or more of said alkoxyamine groups of formula (I) are pendant from a polymer backbone, said method further comprising heating said polymer backbone having one or more pendant alkoxyamine groups of formula (I) above a thermal dissociation temperature of said one or more pendant alkoxyamine groups, in the presence of a second monomer, to thereby form a graft copolymer by controlled growth free radical polymerization initiated by a radical derived from X.

3. The method of claim 2, further comprising a third stage of heating said graft copolymer in the presence of a third monomer to form a block copolymer on the grafted chains of the graft polymer by controlled growth free radical polymerization initiated by a radical derived from X.

4. The method of claim 1, wherein said (co)polymer is prepared from one or more monomers, wherein at least one of the monomers is an alkoxyamine of of formula (I).

5. The method of claim 2 wherein the grafted chains are random or gradient copolymers of a mixture of two or more monomers.

6. The method of claim 1 wherein said (co)polymer is a random or gradient copolymer formed from a mixture of two or more monomers.

7. The method of claim 2, wherein the polymer backbone of the first stage is a homopolymer, block polymer, random or gradient polymer and the graft copolymer formed is a homopolymer, block polymer, random or gradient polymer.

8. The method of claim 1 wherein the polymerization is conducted in a non-polymerizable medium.

9. The method of claim 1, wherein the compound that reacts with, or complexes, the stable free radical of formula (II), generates a free radical at the polymerization temperature.

10. The method of claim 1 wherein the compound that reacts with, or complexes, the stable free radical of formula (II) is a radical initiator having a long half-life time at the polymerization temperature.

11. The method of claim 10, wherein the radical initiator having a long half-life time is an initiator with a half-life time of from 6 to 15 hours at polymerization temperature.

12. The method of claim 11, wherein said half-life time is from 8 to 10 hours at polymerization temperature.

13. The method of claim 10, wherein said radical initiator is a member selected from the group consisting of dicumyl peroxide, di-t-butyl peroxide, di-t-amyl peroxide and t-butyl hydroperoxide.

14. The method of claim 1, comprising sequentially adding a second unsaturated monomer and heating so as to form a block on each (co)polymer segment in conjunction with the polymer of the first monomer.

15. The method of claim 1, wherein said (co)polymer has functional terminal groups which are located at one end of the (co)polymer chains and initiator residues located on the other end of the (co)polymer chains.

16. The method of claim 15, wherein the compound of formula (II) is a nitroxide residue and reacts with the growing polymer chains further comprising:

removing at least one of the nitroxide residues from one or more sites along the (co)polymer and allowing at least one of the nitroxide residues to react with a second radical, Y, forming a compound of the following formula:

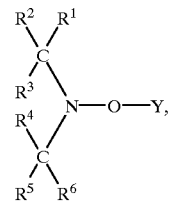

where R1, R2, R3, R4, R5 and R6 are defined above.

17. A method of claim 16, wherein said one or more sites along the (co)polymer is modified to provide a new functional group at the location of removal of the nitroxide residue.

18. A method for the production of a (co)polymer by free radical polymerization of an unsaturated monomers, comprising:

heating to a polymerization temperature the unsaturated monomers in the presence of a free radical initiator comprising an X group, and a stable free radical according to the formula (II)

(II)

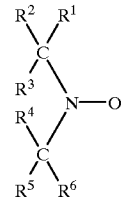

to form growing polymer chains, wherein the free radical initiator comprises a carbon atom, X represents a group having at least one carbon atom and is capable of polymerizing the unsaturated monomer by free radical polymerization, $R^1$, $R^2$, $R^5$ and $R^6$ are the same or different straight chain or branched substituted or unsubstituted alkyl groups of a length sufficient to provide steric hindrance and weakening of a bond between the oxygen in formula II and a carbon atom and $R^3$ and $R^4$ represents the same or different straight chain or branched substituted alkyl groups or $R^3CNCR^4$ may be part of a cyclic or heterocyclic structure which may have fused with it another saturated or aromatic ring, the cyclic structure or aromatic ring being optionally substituted and, a compound that will react with the stable free radical of formula (II) to maintain a constant polymerization rate as the number of growing chains are reduced through termination reactions.

19. The method of claim 18, wherein the (co)polymer being formed is a graft copolymer, and wherein one or more of said alkoxyamine groups of formula (I) are pendant from a polymer backbone, said method further comprising heating said polymer backbone having one or more pendant alkoxyamine groups of formula (I) above a thermal dissociation temperature of said one or more pendant alkoxyamine groups, in the presence of a second monomer, to thereby form a graft copolymer by controlled growth free radical polymerization initiated by a radical derived from X.

20. The method of claim 19, further comprising a third stage of heating said graft copolymer in the presence of a third monomer to form a block copolymer on the grafted chains of the graft polymer by controlled growth free radical polymerization initiated by a radical derived from X.

21. The method of claim 18, wherein said (co)polymer is prepared from one or more monomers wherein at least one of the monomers contains the alkoxyamine group of formula (I).

22. The method of claim 19 wherein the grafted chains are random or gradient copolymers of a mixture of two or more monomers.

23. The method of claim 18 wherein said (co)polymer is a random or gradient copolymer formed from a mixture of two or more monomers.

24. The method of claim 19, wherein the polymer backbone of the first stage is a homopolymer, block polymer, random or gradient polymer and the graft copolymer formed is a homopolymer, block polymer, random or gradient polymer.

25. The method of claim 18 wherein the polymerization is conducted in a non-polymerizable medium.

26. The method of claim 18, wherein the compound that reacts with, or complexes, the stable free radical of formula (II), generates a free radical at the polymerization temperature.

27. The method of claim 18 wherein the compound that reacts with, or complexes, the stable free radical of formula (II) is a radical initiator having a long half-life time at the polymerization temperature.

28. The method of claim 27, wherein the radical initiator having a long half-life time is an initiator with a half-life time of from 6 to 15 hours at the polymerization temperature.

29. The method of claim 28, wherein said half-life time is from 8 to 10 hours at the polymerization temperature.

30. The method of claim 27, wherein said radical initiator is selected from the group consisting of dicumyl peroxide, di-t-butyl peroxide, di-t-amyl peroxide and t-butyl hydroperoxide.

31. The method of claim 18, comprising sequentially adding a second unsaturated monomer and heating so as to form a block on each (co)polymer segment in conjunction with the polymer of the first monomer.

32. The method of claim 18, wherein said (co)polymer has functional terminal groups which are located at one end of the (co)polymer and initiator residues located on the other end of the (co)polymer.

33. The method of claim 32, wherein the compound of formula (II) is a nitroxide residue and reacts with the growing (co)polymer further, comprising:

removing the nitroxide residues from one or more sites along the (co)polymer and allowing the nitroxide residues to react with a second radical, Y, forming a compound of the following formula:

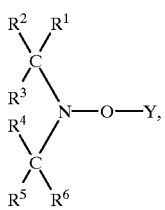

where R1, R2, R3, R4, R5 and R6 are defined above.

34. The method of claim 33, wherein said one or more sites along the (co)polymer chains are modified to provide a new functional group at the location of removal of the nitroxide residue.

35. A method for the production of a (co)polymer by free radical polymerization of an unsaturated monomer, comprising:

heating a polymerization medium comprising the monomer, a radical initiator having at least one carbon atom and being capable of polymerizing the unsaturated monomer by free radical polymerization, and a stable free radical according to the formula (II) to a temperature lower than a polymerization temperature for the polymerization medium;

(II)

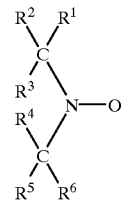

heating the polymerization medium to a polymerization temperature;

adding a compound that will react with, or complex, the stable free radical of formula (II) to thereby maintain a substantially constant polymerization rate throughout the polymerization process.

36. The method of claim 35, wherein the (co)polymer being formed is a graft copolymer, and wherein one or more of said alkoxyamine groups of formula (I) are pendant from a polymer backbone, said method further comprising heating said polymer backbone having one or more pendant alkoxyamine groups of formula (I) above a thermal dissociation temperature of said one or more pendant alkoxyamine groups, in the presence of a second monomer, to thereby form a graft copolymer by controlled growth free radical polymerization initiated by a radical derived from X.

37. The method of claim 36, further comprising heating said graft copolymer in the presence of a third monomer to form a block copolymer on the grafted chains of the graft polymer by controlled growth free radical polymerization initiated by a radical derived from X.

38. The method of claim 35, wherein said (co)polymer is prepared from one or more monomers wherein at least one of the monomers contains the alkoxyamine group of formula (I).

39. The method of claim 36 wherein the grafted chains are random or gradient copolymers of a mixture of two or more monomers.

40. The method of claim 35 wherein said (co)polymer is a random or gradient copolymer formed from a mixture of two or more monomers.

41. The method of claim 36, wherein the polymer backbone of the first stage is a homopolymer, block polymer, random or gradient polymer and the graft copolymer formed is a homopolymer, block polymer, random or gradient polymer.

42. The method of claim 35 wherein the polymerization is conducted in a non-polymerizable medium.

43. The method of claim 35, wherein the compound that reacts with, or complexes, the stable free radical of formula (II), generates a free radical at the polymerization temperature.

44. The method of claim 35 wherein the compound that reacts with, or complexes, the stable free radical of formula (II) is a radical initiator having a long half-life time at the polymerization temperature.

45. The method of claim 44, wherein the radical initiator having a long half-life time is an initiator with a half-life time of from 6 to 15 hours at the polymerization temperature.

46. The method of claim 45, wherein said half-life time is from 8 to 10 hours at the polymerization temperature.

47. The method of claim 44, wherein said radical initiator is selected from the group consisting of dicumyl peroxide, di-t-butyl peroxide, di-t-amyl peroxide and t-butyl hydroperoxide.

48. The method of claim 35, comprising sequentially adding a second unsaturated monomer and heating so as to form a block on each (co)polymer segment in conjunction with the polymer of the first monomer.

49. The method of claim 35, wherein said (co)polymer has functional terminal groups which are located at one end of the (co)polymer and initiator residues located on the other end of the (co)polymer.

50. The method of claim 49, wherein the compound of formula (II) is a nitroxide residue and reacts with the growing (co)polymer, further comprising:

removing at least one of the nitroxide residues from one or more sites along the (co)polymer and allowing at least one of the nitroxide residues to react with a second radical, Y, forming a compound of the following formula:

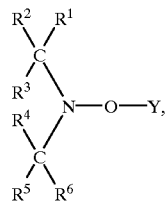

where R1, R2, R3, R4, R5 and R6 are defined above.

51. The method of claim 50, wherein said one or more sites along the (co)polymer are modified to provide a new functional group at the location of removal of the nitroxide residue.

52. The method of claim 18, wherein heating the unsaturated monomers in the presence of a free radical initiators, X., and a stable free radical according to the formula (II) comprises reacting a polymer with a non-carbon center free radical in the presence of the stable free radical of formula (I).

53. A method of rate enhancement of a free radical polymerization process, comprising:

polymerizing radically polymerizable monomers with a free radical initiator and growing polymer chains, in the presence of stable free radicals, wherein the free radical polymerization process is controlled by the reversible reaction of the stable free radicals with the growing polymer chains to form dormant polymer chains; and maintaining an approximate molar ratio of the sum of stable free radicals and dormant polymer chains to the sum of free radical initiators and growing polymer chains by adding or forming scavenging radicals, wherein the scavenging radicals react with the stable free radicals to reduce the number of the stable free radicals available for controlling the free radical polymerization process as the number of growing chains is reduced by termination reactions.

* * * * *

UNITED STATES PATENT AND TRADEMARK OFFICE
CERTIFICATE OF CORRECTION

PATENT NO. : 6,288,186 B1
DATED : September 5, 2001
INVENTOR(S) : Matyjasezeski et al.

It is certified that error appears in the above-identified patent and that said Letters Patent is hereby corrected as shown below:

<u>Title page,</u>
Item [57], ABSTRACT,
Line 8, delete ".";

<u>Column 2,</u>
Line 29, delete "only few" and substitute there for -- only a few --;

<u>Column 9,</u>
Line 51, delete "(";

<u>Column 10,</u>
Line 18, delete "=" and substitute there for -- $\leq$ --;
Line 19, delete "then" and substitute there for -- than --; and
Line 32, delete "for".

Signed and Sealed this

Tenth Day of September, 2002

*Attest:*

JAMES E. ROGAN
*Attesting Officer*   *Director of the United States Patent and Trademark Office*